United States Patent [19]

Konrad et al.

[11] 4,322,212

[45] Mar. 30, 1982

[54] OXIDATION HAIR DYES COMPRISING SUBSTITUTED BENZOTRIAZOLES

[75] Inventors: Günther Konrad, Hilden; Edgar Lieske, Düsseldorf, both of Fed. Rep. of Germany

[73] Assignee: Henkel Kommanditgesellschaft auf Aktien, Düsseldorf-Holthausen, Fed. Rep. of Germany

[21] Appl. No.: 209,585

[22] Filed: Nov. 24, 1980

[30] Foreign Application Priority Data

Dec. 13, 1979 [DE] Fed. Rep. of Germany ....... 2950032

[51] Int. Cl.$^3$ ............................................... A61K 7/13
[52] U.S. Cl. ........................................... 8/407; 8/408; 8/409; 8/406; 8/423
[58] Field of Search ................... 8/407, 409, 573, 570, 8/406, 408, 423

[56] References Cited

U.S. PATENT DOCUMENTS

| | | | |
|---|---|---|---|
| 2,334,348 | 11/1943 | Miglarese | 167/90 |
| 2,671,775 | 3/1954 | Hanhart | 260/155 |
| 3,630,655 | 12/1971 | Berth et al. | 8/11 |
| 4,003,699 | 1/1977 | Rose et al. | 8/10.2 |
| 4,104,020 | 8/1978 | Rose | 8/10.2 |

*Primary Examiner*—Donald B. Moyer
*Attorney, Agent, or Firm*—Hammond & Littell, Weissenberger and Muserlian

[57] ABSTRACT

This invention is directed to compositions of the developer-coupler type for the dyeing of hair, consisting essentially of substituted benzotriazoles as coupling components and, as developer components, the conventional components used in oxidation dyes.

11 Claims, No Drawings

OXIDATION HAIR DYES COMPRISING SUBSTITUTED BENZOTRIAZOLES

FIELD OF THE INVENTION

This invention is directed to oxidation hair dyes. More specifically, this invention is directed to agents for the oxidative dyeing of hair that are based upon substituted benzotriazoles as coupling components.

BACKGROUND OF THE INVENTION

Dyes known as oxidation dyes, which are produced by oxidative coupling of a developer component with a coupling component, are preferred due to their intense colors and very good fastness. Nitrogen bases such as p-phenylenediamine derivatives, diaminopyridines, 4-aminopyrazolone derivatives, and heterocyclic hydrazones are generally used as developer substances. Phenols, naphthols, resorcinol derivatives, and pyrazolones are useful as coupling components.

Good oxidation dyestuff components must meet the following requirements:

They must produce the desired color nuances in sufficient intensity during oxidative coupling with the respective developer or coupling component. Also, they must possess a capacity for being absorbed by human hair, which capacity ranges from sufficient to very good; and, in addition, they should be toxicologically and dermatologically safe. The production of the strongest possible color shades closely corresponding to the natural hair color nuances is also important. Further, the general stability of the dyestuff produced as well as their fastness to light and to washing and their thermostability, have very special significance for the prevention of color shifts from the original color nuance or even a change in color to different shades.

Thus, the search for suitable oxidation hair dyes includes the task of finding the proper components that meed the above-mentioned prerequisites in an optimal fashion.

OBJECTS OF THE INVENTION

It is an object of the invention to provide novel hair dyestuffs.

It is also an object of the invention to provide agents for the oxidative dyeing of hair that are based upon substituted benzotriazoles as coupling components.

It is a further object of the invention to provide a process for dyeing hair wherein a novel hair dyestuff is employed.

These and other objects of the invention will become more apparent in the discussion below.

DESCRIPTION OF THE INVENTION

Applicants have found novel hair dyestuffs that satisfy the above-mentioned requirements. The hair dyestuffs are based upon oxidation dyes comprising substituted benzotriazoles of the formula

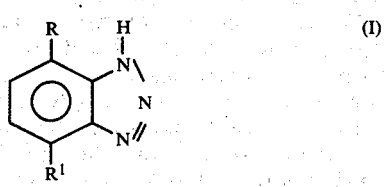

wherein R and $R^1$ each represent a hydrogen atom or an amino group, with the proviso that at least one of R and $R^1$ is an amino group, adducts thereof with from 1 to 4 moles of ethylene oxide per mole of substituted benzotriazole, or salts thereof with inorganic or organic acids, as coupling components and the developer components normally used in oxidation hair dyestuffs. Such hair dyestuffs can meet the above-mentioned requirements to an especially high degree.

Upon the use of substituted benzotriazoles as coupling components together with developers generally used for oxidation hair dyes, the resulting hair dyes yield very intense and light-fast color nuances ranging from dark blonde to brown to brown-violet, and thus such use represents a considerable expansion of the possibilities in oxidation hair dyeing. In addition, substituted benzotriazoles are characterized by very good fastness characteristics of the resulting colors, good solubility in water, good shelf-life, and toxicological as well as dermatological safety.

The substituted benzotriazoles to be used as coupling components according to the invention can be used as such or in the form of their salts with inorganic or organic acids. Useful salts include, for example, chlorides, sulfates, phosphates, acetates, propionates, lactates, citrates, and the like.

The substituted benzotriazoles of Formula I represent compounds known from the literature, the preparation of which is described by K. Fries, H. Güterbock, and H. Kuhn in the publication "Studies in the Azimidobenzene Series" in the Annals of Chemistry 511: 229, 1934, and by S. Angeloni et al. in Tetrahedron 28: 313, 1972. For example, hydrogenation of the 4,7-dioximino derivative of benzotriazole, in methanol in the presence of a catalyst, yields 4,7-diaminobenzotriazole, which can also be prepared by hydrogenation of 4-amino-7-phenylazobenzotriazole. Also, 4-aminobenzotriazole can be prepared by the catalytic reduction of 4-nitrobenzotriazole. There is no mention of the suitability of substituted benzotriazoles as agents for hair dyes. The preparation of the adducts of substituted benzotriazoles with from 1 to 4 moles of ethylene oxide takes place according to generally known methods of ethoxylation of compounds with active hydrogen atoms by reaction of the aminobenzotriazole derivatives with ethylene oxide in the autoclave at 100° C.

Coupling components useful according to the invention include, for example, 4(7)-aminobenzotriazole, 4,7-diaminobenzotriazole, 4(7)-aminobenzotriazole+1 mole ethylene oxide, 4(7)-aminobenzotriazole+2 moles ethylene oxide, 4(7)-aminobenzotriazole+3 moles ethylene oxide, 4(7)-aminobenzotriazole+4 moles ethylene oxide, 4,7-diaminobenzotriazole+1 mole ethylene oxide, 4,7-diaminobenzotriazole+2 moles ethylene oxide, 4,7-diaminobenzotriazole+3 moles ethylene oxide, and 4,7-diaminobenzotriazole+4 moles ethylene oxide.

The developer components to be used according to the invention are those that are conventionally used in oxidatively coupled dyestuffs. Examples of such developer components include primary aromatic amines with an additional functional group in the p-position, such as p-phenylenediamine, p-toluenediamine, p-aminophenol, N-methyl-p-phenylenediamine, N,N-dimethyl-p-phenylenediamine, N,N-diethyl-2-methyl-p-phenylenediamine, N-ethyl-N-hydroxyethyl-p-phenylenediamine, chloro-p-phenylenediamine, N,N-bis-hydroxyethylamino-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, and 6-methoxy-3-methyl-p-phenylenediamine, and other compounds of this type which also contain one or more additional functional groups such as hydroxyl groups, amino groups, or $NHR^2$ or $NR_2^2$ groups, in which $R^2$ represents an alkali metal or a hydroxyalkyl moiety with from 1 to 4 carbon atoms. Diaminopyridine derivatives, heterocyclic hydrazone derivatives such as 1-methyl-pyrrolidon(2)-hydrazone, 4-amino-pyrazolone derivatives such as 4-amino-1-phenyl-3-carbamoylpyrazolone-5, and N-butyl-N-sulfobutyl-p-phenylenediamine are additional examples of useful developer components.

Further developer components that can be combined with 3-amino-2-methylphenol include tetraaminopyrimidines of the general formula

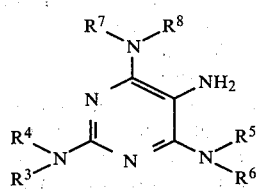

wherein $R^3$ to $R^8$ may each be a hydrogen atoms; an alkyl moiety with from 1 to 4 carbon atoms; or the radical $-(CH_2)_nX$ in which n is an integer of from 1 to 4 and X is selected from the group consisting of a hydroxyl group, a halogen atom, and $-NH^9R^{10}$ in which $R^9$ and $R^{10}$ are each a hydrogen atom or an alkyl group having from 1 to 4 carbon atoms or together with the nitrogen atom $R^9$ and $R^{10}$ form a member selected from the group consisting of a 5 or 6 membered heterocyclic ring optionally containing an additional nitrogen atom or oxygen atom in the ring, as well as their inorganic or organic salts. See, for example, U.S. Pat. No. 4,003,699.

The tetraaminopyrimidines to be used as developer components may be used as such or in the form of their salts with inorganic or organic acids, such as, for example, chlorides, sulfates, phosphates, acetates, propionates, lactates, citrates, and the like.

Developer substances suitable for combination with the 3-amino-2-methylphenol used as coupling component according to the invention include, for example, the following:
2,4,5,6-tetraaminopyrimidine,
4,5-diamino-2,6-bismethylaminopyrimidine,
2,5-diamino-4,6-bismethylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidinopyrimidine,
4,5-diamino-6-methylamino-2-piperidinopyrimidine,
2,4,5-triamino-6-piperidinopyrimidine,
2,4,5-triamino-6-anilinopyrimidine,
2,4,5-triamino-6-benzylaminopyrimidine,
2,4,5-triamino-6-benzylidenaminopyrimidine,
4,5,6-triamino-2-piperidinopyrimidine,
2,4,6-trismethylamino-5-aminopyrimidine,
2,4,5-triamino-6-di-n-propylaminopyrimidine,
2,4,5-triamino-6-morpholinopyrimidine,
2,5,6-triamino-4-dimethylaminopyrimidine,
4,5,6-triamino-2-morpholinopyrimidine,
2,4,5-triamino-6-$\beta$-hydroxyethylaminopyrimidine,
4,5,6-triamino-2-$\beta$-amino-ethylaminopyrimidine,
2,5,6-triamino-4-$\beta$-methylamino-ethylaminopyrimidine,
2,5-diamino-4,6-bis-$\gamma$-diethylamino-propylaminopyrimidine,
4,5-diamino-2-methylamino-6-$\beta$-hydroxyethylaminopyrimidine,
5-amino-2,4,5-triethylaminopyrimidine, and
2,4-bis-$\beta$-hydroxyethylamino-6-anilino-5-aminopyrimidine.

In the hair dyestuffs according to the invention, the coupling and developer components generally are used in approximately equimolar amounts. Although the equimolar use proves suitable, it is not disadvantageous to add the coupling component in a certain excess or deficiency. For example, the coupling and developer components can be present in a molar range of from about 2:1 to 1:2, a 10% or less excess or deficiency being preferred.

In addition, it is not necessary that the developer component and the coupling substance are homogenous or pure products. On the contrary, the developer component may consist of mixtures of the developer compounds to be used according to the invention, and the coupling substance may be in the form of mixtures of substituted benzotriazoles according to the invention. Furthermore, the hair dyestuffs according to the invention may also contain, if desired, conventional, directly applicable dyes in the mixture, provided that such are necessary for the creation of certain color nuances.

The oxidative coupling, that is, the development of the dye, can in principle be carried out with atmospheric oxygen, as is done with other oxidation hair dyestuffs also. However, chemical oxidation agents are advantageously employed. Particularly suitable as such oxidation agents are hydrogen peroxide or its addition compounds with urea, melamine, or sodium borate as well as mixtures of such hydrogen peroxide adducts with potassium peroxydisulfate.

The dyes according to the invention are incorporated into respective cosmetic preparations such as creams, emulsions, gels, or also simple solutions for their use and are mixed with one of the mentioned oxidation agents immediately before application to the hair. The concentration of the coupling developer combination in such dyes is from about 0.2 to 5 percent by weight, preferably from about 1 to 3 percent by weight, based on the total weight of the preparation.

For the preparation of creams, emulsions, or gels, the dye components are mixed with the other components normally used in such preparations. Such additional components include, for example, wetting or emulsifying agents of the anionic or nonionic type such as alkylbenzenesulfonates, sulfates of fatty alcohols, higher alkylsulfonates, alkanolamines of fatty acids, adducts of ethylene oxide with fatty alcohols, thickeners such as methyl cellulose, starch, higher fatty alcohols, paraffin oil, and fatty acids, and perfume oils and hair-conditioning and grooming agents such as pantothenic acid and cholesterol. The mentioned additives are added in the amounts normal for these purposes. For example, wetting and emulsifying agents can be present in concentrations of from about 0.5 to 30 percent by weight, preferably from about 1 to 15 percent by weight, and thickeners can be present in concentrations of from about 0.1 to 25 percent by weight, preferably from about 1 to 15 percent by weight, based, respectively, on the weight of the total preparation.

The dye according to the invention can be applied in a weakly acid, neutral or particularly alkaline medium at a pH of 8 to 10, regardless of whether it is a solution, an emulsion, a cream, or a gel. The application temperatures range from about 15° to 40° C., preferably at room temperature. After the dye is allowed to react for approximately 30 minutes, the preparation is removed by rinsing from the hair to be dyed. Then the hair is washed with a mild shampoo and dried.

The following examples are intended to illustrate the invention and are not to be construed as limiting the invention thereto.

EXAMPLES

Coupling components:

The following products were used as substituted benzotriazoles according to the invention to serve as coupling substances in the examples below:
- A: 4(7)-aminobenzotriazole (mixture of the tautomers)
- B: 4,7-diaminobenzotriazole
- C: 4(7)-aminobenzotriazole + 1 mole ethylene oxide
- D: 4(7)-aminobenzotriazole + 2 moles ethylene oxide
- E: 4(7)-aminobenzotriazole + 4 moles ethylene oxide The ethylene oxide adducts were obtained by heating 4(7)-aminobenzotriazole with the respective amounts of ethylene oxide in ethanol in the autoclave at 100° C. for 6 hours. The compounds obtained were in the form of dark brown oils.

Developer components:

The following compounds were used as developer components in the examples below:
- E-1: 2,4,5,6-tetraminopyrimidine
- E-2: p-toluylene diamine
- E-3: N,N-bis-(2-hydroxyethylamino)-m-phenylenediamine
- E-4: 2-methylamino-4,5,6-triaminopyrimidine
- E-5: 1-phenyl-3-carbamoyl-4-aminopyrazolone
- E-6: 2,5-diaminoanisole
- E-7: 2-chloro-p-phenylenediamine.

Procedure:

The hair dyes according to the invention were used in the form of a cream emulsion. For this, 0.01 mole of the developer substances and substituted benzotriazoles listed in the table below were worked into the emulsion containing
- 10 parts by weight of fatty alcohols having 12 to 18 carbon atoms,
- 10 parts by weight of fatty alcohol sulfate (sodium salt) having 12 to 18 carbon atoms, and
- 75 parts by weight of water.

Then the pH of the emulsion was adjusted to 9.5 with ammonia, and the emulsion was made up to 100 parts by weight with water. Oxidative coupling was carried out with a 1% hydrogen peroxide solution acting as oxidation agent, 10 parts by weight of the hydrogen peroxide solution being added to 100 parts by weight of the emulsion. The particular dyeing cream, with or without additional oxidation agent, was applied to human hair which was 90% grey and which had not been specially pretreated, and the cream was left on the hair for 30 minutes. After completion of the dyeing process, the hair was washed out with a regular shampoo and then dried. The colorations obtained by this process can be found in the table below.

TABLE

| Example | Developer | Coupler | Color Shade Obtained with 1% H$_2$O$_2$ Solution |
|---|---|---|---|
| 1 | E-1 | A | grey-brown |
| 2 | E-2 | A | dark violet |
| 3 | E-1 | B | fawn-colored |
| 4 | E-2 | B | purple-grey |
| 5 | E-1 | C | light-brown |
| 6 | E-2 | C | brown-violet |
| 7 | E-3 | C | blue-grey |
| 8 | E-1 | D | golden brown |
| 9 | E-2 | D | dark red-brown |
| 10 | E-3 | D | blue-grey |
| 11 | E-6 | D | blue-grey |
| 12 | E-7 | D | grey-brown |
| 13 | E-4 | D | nougat-colored |
| 14 | E-1 | E | dark blond |
| 15 | E-2 | E | dark brown |
| 16 | E-3 | E | blue-grey |
| 17 | E-4 | E | grey-brown |
| 18 | E-5 | E | brown-grey |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A composition of the developer-coupler type for the dyeing of human hair, consisting essentially of at least one substituted benzotriazole of the formula

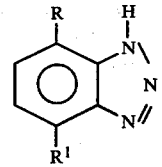

wherein R and R$^1$ each respresent a hydrogen atom or an amino group, with the proviso that at least one of R and R$^1$ is an amino group, an adduct thereof with from 1 to 4 moles of ethylene oxide per mole of substituted benzotriazole, or a salt thereof, as coupling component, and, as developer component, one or more of the conventional developer components used in oxidation dyes, the molar ratio of the coupler to the developer being from 2:1 to 1:2.

2. The composition of claim 1 which additionally contains conventional additives selected from the group consisting of conventional couplers and conventional directly absorbing dyes.

3. The composition of claim 1 wherein the compocition comprises from about 0.2 to 5 percent by weight of developer-coupler combination.

4. The composition of claim 3 wherein the composition comprises from about 1 to 3 percent by weight of developer-coupler combination.

5. A process for the dyeing of hair comprising applying to said hair, at temperatures ranging substantially from about 15° C. to 40° C. for a time sufficient to effect dyeing through oxidation, an effective amount of the developer-coupler composition according to claim 1 in an aqueous medium.

6. The process for the dyeing of hair of claim 5 wherein the oxidation is effected by the action of a chemical oxidation agent.

7. The process of claim 6, wherein the chemical oxidation agent is selected from the group consisting of hydrogen peroxide or its addition compounds with urea, melamine, or sodium borate, and mixtures thereof with potassium peroxydisulfate.

8. The composition of claim 1, wherein the developer component comprises one or more compunds selected from the group consisting of
p-toluylene diamine,
2,4,5,6-tetraaminopyrimidine,
4,5-diamino-2,6-bismethylaminopyrimidine,
2,5-diamino-4,6-bismethylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidinopyrimidine,
4,5-diamino-6-methylamino-2-piperidinopyrimidine,
2,4,5-triamino-6-piperidinopyrimidine,
2,4,5-triamino-6-anilinopyrimidine,
2,4,5-triamino-6-benzylaminopyrimidine,
2,4,5-triamio-6-benzylidenaminopyrimidine,
4,5,6-triamino-2-piperidinopyrimidine,
2,4,6-trismethylamino-6-aminopyrimidine,
2,4,5-triamino-6-di-n-propylaminopyrimidine,
2,4,5-triamino-6-morpholinopyrimidine,
2,5,6-triamino-4-dimethylaminopyrmidine,
4,5,6-triamino-2-morpholinopyrimidine,
2,4,5-triamino-6-$\beta$-hydroxyethylaminopyrimidine,
4,5,6-triamino-2-$\beta$-amino-ethylaminopyrimidine,
2,5,6-triamino-4-$\beta$-methylamino-ethylaminopyrimidine,
2,5-diamino-4,6-bis-gamma-diethylamino-propylaminopyrimidine,
4,5-diamino-2-methylamino-6-$\beta$-hydroxy-ethylaminopyrimidine,
5-amino-2,4,5-triethylaminopyrimidine,
2,4-bis-$\beta$-hydroxyethylamino-6-anilino-5-aminopyrimidine,
N,N-bis-(2-hydroxyethylamino)-m-phenylenediamine,
2-methylamino-4,5,6-triaminopyrimidine,
1-phenyl-3-carbamoyl-4-aminopyrazolone,
2,5-diaminoanisole, and
2-chloro-p-phenylenediamine.

9. The composition of claim 1 which comprises
  (1) from about 0.2 to 5 percent by weight of developer-coupler combination;
  (2) from about 0.5 to 30 percent by weight of wetting and emulsifying agents;
  (3) from about 0.1 to 25 percent by weight of thickeners; and
  (4) the balance water.

10. A process for the dyeing of hair comprising applying to said hair, at temperatures ranging substantially from about 15° and 40° C. at a pH of from about 8 to 10 for a time sufficient to effect dyeing through oxidation, an effective amount of the aqueous developer-coupler composition according to claim 8.

11. The process for the dyeing of hair of claim 10, wherein the oxidation is also effected by the action of a chemical oxidation agent selected from the group consisting of hydrogen peroxide and its addition agents with urea, melamine, or sodium borate, and mixtures thereof with potassium peroxydisulfate.

* * * * *